(12) United States Patent
Ghassan

(10) Patent No.: US 8,204,695 B2
(45) Date of Patent: *Jun. 19, 2012

(54) TECHNIQUES FOR IDENTIFYING, CONFIRMING, MAPPING, AND CATEGORIZING POLYMERS

(75) Inventor: Ghandour Ghassan, Atherton, CA (US)

(73) Assignee: Affymetrix, Inc., Santa Clara, CA (US)

( * ) Notice: Subject to any disclaimer, the term of this patent is extended or adjusted under 35 U.S.C. 154(b) by 731 days.

This patent is subject to a terminal disclaimer.

(21) Appl. No.: 11/483,266

(22) Filed: Jul. 7, 2006

(65) Prior Publication Data

US 2007/0043517 A1 Feb. 22, 2007

Related U.S. Application Data

(63) Continuation of application No. 09/229,060, filed on Jan. 11, 1999, now Pat. No. 7,099,777, which is a continuation-in-part of application No. 09/148,210, filed on Sep. 5, 1998, now abandoned.

(60) Provisional application No. 60/057,957, filed on Sep. 5, 1997.

(51) Int. Cl.
G06F 19/00 (2011.01)
G11C 17/00 (2006.01)
C12Q 1/68 (2006.01)

(52) U.S. Cl. ............... 702/20; 365/94; 435/6.11

(58) Field of Classification Search ............... None
See application file for complete search history.

(56) References Cited

U.S. PATENT DOCUMENTS

| 5,549,805 A | 8/1996 | Middendorf et al. |
| 5,858,659 A * | 1/1999 | Sapolsky et al. ............... 435/6 |
| 7,099,777 B1 * | 8/2006 | Ghandour ............... 702/20 |

FOREIGN PATENT DOCUMENTS

| GB | 2 166 445 | 5/1986 |
| WO | WO 97/29212 | 8/1997 |

OTHER PUBLICATIONS

Conner et al. Detection of sickle cell beta-s-globin allele by hybridization with synthetic oligonucleotides Proceeding of the National Academy of Sciences, USA vol. 80, pp. 278-282 (1983).*

Hau, P. P. et al. "A biostatistical study into the efficiency of individualism using nonisotopic chemiluminescent-enhanced NICE multilocus DNA probes," Electrophoresis, vol. 18, Oct. 1997, pp. 1916-1922.

Jeffreys, A. J. et al. "Amplification of human minisatellites by the polymerase chain reaction: towards DNA fingerprinting of single cells," Nucleic Acids Res., vol. 16, Dec. 9, 1988, pp. 10953-10971.

Labrune, P. et al. "Single-strand conformation polymorphism for detection of mutations and base substitutions in phenylketonuria," Am.J.Hum.Genet., vol. 48, Jun. 1991, pp. 1115-1120.

Morrison, L. E. et al. "Two-color ratio-coding of chromosome targets in fluorescence in situ hybridization: quantitative analysis and reproducibility," Cytometry, 27, Apr. 1, 1997, pp. 314-326.

Tabernero, M. D. et al. "Clinical, biological, and immunophenotypical characteristics of B-cell chronic lymphocytic leukemia with trisomy 12 by fluorescence in situ hybridization," Cytometry, vol. 22, Sep. 15, 1995, pp. 217-222.

Wang, D. G. et al. "Large-scale identification, mapping, and genotyping of single-nucleotide polymorphisms in the human genome," Science, vol. 280, May 15, 1998, pp. 1077-1082.

* cited by examiner

*Primary Examiner* — John S Brusca
(74) *Attorney, Agent, or Firm* — Sandra E. Wells

(57) ABSTRACT

Systems and methods for identifying, confirming, mapping, and categorizing sample polymers, such as nucleic acid sequences, are provided. An estimation of the fraction of first and second polymers in a sample of polymers can be calculated by inputting a first hybridization value indicative of hybridization affinity of the sample of polymers to polymers probes that are complementary to the first polymer and inputting a second hybridization value indicative of hybridization affinity of the sample of polymers to polymers probes that are complementary to the second polymer. The estimation of the fraction of the first and second polymers in the sample of polymers can then be calculated by dividing the first hybridization value by a sum of the first and second hybridization values. Estimations of the fractions of alleles in a sample can be clustered to form a fraction pattern usable for identifying, confirming, mapping, and genotyping sample nucleic acids.

6 Claims, 11 Drawing Sheets

| d | −2 | −1 | 0 | +1 | +2 |
|---|---|---|---|---|---|
|   | T | C | G/A | G | C |

A-ALLELE TILING

| | −2 T | −1 C | 0 G/A | +1 G | +2 C |
|---|---|---|---|---|---|
| T | Ma | Ma | PMb | Ma | PMa |
| G | Ma | PMa | M* | Ma | PMa |
| C | Ma | Ma | PMa | PMa | Ma |
| A | PMa | Ma | M* | Ma | Ma |

B-ALLELE TILING

| | −2 T | −1 C | 0 G/A | +1 G | +2 C |
|---|---|---|---|---|---|
| T | Mb | Mb | PMb | Mb | Mb |
| G | Mb | PMb | M* | Mb | PMb |
| C | Mb | Mb | PMa | PMb | Mb |
| A | PMb | Mb | M* | Mb | Mb |

|  | 375 | 376 | 377 MARKER | 378 STRAND | 379 NN | 380 NA | 381 NH | 382 NB | 383 PA | 384 PH | 385 PB |
|---|---|---|---|---|---|---|---|---|---|---|---|
|  |  | 1 | SGC30038.42 | Z | 1 | 20 | 9 | 11 | 97 | 25 | 3 |
|  |  | 2 | SGC30055.32 | A | 0 | 8 | 26 | 7 | 99 | 61 | 1 |
|  |  | 3 | SGC30078.97 | A | 0 | 35 | 5 | 1 | 80 | 33 | 1 |
|  |  | 4 | SGC30122.74 | A | 0 | 11 | 20 | 10 | 89 | 42 | 8 |
|  |  | 5 | SGC30160.57 | Z | 0 | 40 | 1 | 0 | 96 | 54 | . |
|  |  | 6 | SGC30207.50 | A | 0 | 30 | 10 | 1 | 100 | 38 | 0 |
|  |  | 7 | SGC30272.71 | Z | 0 | 27 | 13 | 1 | 93 | 35 | 5 |
|  |  | 8 | SGC30349.71 | A | 0 | 22 | 15 | 4 | 89 | 54 | 16 |
|  |  | 9 | SGC30374.82 | A | 0 | 15 | 17 | 9 | 88 | 49 | 5 |
|  |  | 10 | SGC30386.35 | Z | 0 | 11 | 20 | 10 | 85 | 58 | 4 |
|  |  | 11 | SGC30598.70 | A | 0 | 37 | 4 | 0 | 96 | 52 | . |
|  |  | 12 | SGC30610.99 | Z | 0 | 17 | 19 | 5 | 91 | 51 | 10 |
|  |  | 13 | SGC30612.39 | A | 0 | 40 | 1 | 0 | 93 | 30 | . |
|  |  | 14 | SGC30678.30 | A | 0 | 7 | 13 | 21 | 94 | 52 | 19 |
|  |  | 15 | SGC30689.58 | Z | 0 | 37 | 3 | 1 | 88 | 46 | 4 |
|  |  | 16 | SGC30719.53 | Z | 0 | 24 | 16 | 1 | 96 | 56 | 14 |
|  |  | 17 | SGC30754.66 | Z | 0 | 22 | 15 | 4 | 100 | 48 | 7 |
|  |  | 18 | SGC30813.103 | A | 0 | 14 | 22 | 5 | 89 | 39 | 8 |
|  |  | 19 | SGC30890.87 | Z | 0 | 17 | 23 | 1 | 91 | 40 | 1 |
|  |  | 20 | SGC30895.72 | A | 0 | 7 | 22 | 12 | 88 | 51 | 7 |
|  |  | 21 | SGC30914.75 | A | 0 | 39 | 2 | 0 | 84 | 44 | . |
|  |  | 22 | SGC30938.60 | A | 0 | 8 | 19 | 14 | 88 | 45 | 9 |
|  |  | 23 | SGC30985.75 | A | 0 | 27 | 11 | 3 | 93 | 64 | 47 |
|  |  | 24 | SGC31049.98 | A | 0 | 20 | 17 | 4 | 92 | 60 | 9 |
|  |  | 25 | SGC31070.42 | A | 0 | 13 | 23 | 5 | 89 | 51 | 6 |
|  |  | 26 | SGC31141.40 | A | 0 | 29 | 10 | 2 | 92 | 45 | 16 |
|  |  | 27 | SGC31208.47 | A | 0 | 34 | 6 | 1 | 96 | 46 | 7 |
|  |  | 28 | SGC31224.47 | A | 0 | 37 | 4 | 0 | 97 | 36 | . |
|  |  | 29 | SGC31233.85 | Z | 0 | 7 | 18 | 16 | 97 | 56 | 4 ←391 |
|  |  | 30 | SGC31299.57 | Z | 0 | 2 | 22 | 17 | 99 | 48 | 1 |
|  |  | 31 | SGC31303.117 | A | 0 | 10 | 14 | 17 | 96 | 44 | 4 |
|  |  | 32 | SGC31319.31 | A | 0 | 28 | 12 | 1 | 95 | 54 | 10 |
|  |  | 33 | SGC31324.45 | A | 0 | 31 | 9 | 1 | 88 | 61 | 4 |
|  |  | 34 | SGC31465.84 | A | 1 | 0 | 2 | 38 | . | 61 | 22 |
|  |  | 35 | SGC31480.131 | Z | 0 | 37 | 4 | 0 | 88 | 50 | . |
|  |  | 36 | SGC31493.136 | A | 0 | 23 | 16 | 2 | 93 | 58 | 5 ←393 |
|  |  | 37 | SGC31494.129 | A | 0 | 13 | 17 | 11 | 97 | 71 | 10 |
|  |  | 38 | SGC31534.139 | A | 0 | 31 | 9 | 1 | 86 | 43 | 10 |
|  |  | 39 | SGC31576.106 | A | 0 | 29 | 11 | 1 | 100 | 59 | 0 |
|  |  | 40 | SGC31596.24 | A | 0 | 4 | 20 | 17 | 98 | 38 | 3 ←395 |
|  |  | 41 | SGC31656.66 | A | 0 | 32 | 9 | 0 | 98 | 57 | . |
|  |  | 42 | SGC31729.128 | A | 0 | 28 | 11 | 2 | 96 | 58 | 4 |
|  |  | 43 | SGC31966.61 | A | 0 | 24 | 14 | 3 | 94 | 35 | 1 |
|  |  | 44 | SGC32030.51 | A | 0 | 27 | 12 | 2 | 95 | 31 | 0 |
|  |  | 45 | SGC32060.115 | A | 0 | 1 | 6 | 34 | 93 | 47 | 14 |

*FIG. 8*

TECHNIQUES FOR IDENTIFYING, CONFIRMING, MAPPING, AND CATEGORIZING POLYMERS

This application is a continuation of U.S. patent application Ser. No. 09/229,060, filed Jan. 11, 1999, which is a continuation-in-part of U.S. patent application Ser. No. 09/148,210, filed Sep. 5, 1998, which claims the benefit of U.S. Provisional Application No. 60/057,957, filed Sep. 5, 1997, all of which are hereby incorporated by reference.

GOVERNMENT RIGHTS NOTICE

Portions of the material in this specification arose under the cooperative agreement 70NANABSH1031 between Affymetrix, Inc. and the Department of Commerce through the Advanced Technology Program.

BACKGROUND OF THE INVENTION

The present invention relates to detecting differences in polymers. More specifically, the present invention relates to techniques for identifying, confirming, mapping, and genotyping sample nucleic acid sequences.

Devices and computer systems for forming and using arrays of materials on a chip or substrate are known. For example, PCT applications WO92/10588 and 95/11995, both incorporated herein by reference for all purposes, describe techniques for sequencing or sequence checking nucleic acids and other materials. Arrays for performing these operations may be formed according to the methods of, for example, the pioneering techniques disclosed in U.S. Pat. Nos. 5,445,934, 5,384,261 and 5,571,639, each incorporated herein by reference for all purposes.

According to one aspect of the techniques described therein, an array of nucleic acid probes is fabricated at known locations on a chip. A labeled nucleic acid is then brought into contact with the chip and a scanner generates an image file indicating the locations where the labeled nucleic acids are bound to the chip. Based upon the image file and identities of the probes at specific locations, it becomes possible to extract information such as the nucleotide or monomer sequence of DNA or RNA. Such systems have been used to form, for example, arrays of DNA that may be used to study and detect mutations relevant to genetic diseases, cancers, infectious diseases, HIV, and other genetic characteristics.

The VLSIPS™ technology provides methods of making very large arrays of oligonucleotide probes on very small chips. See U.S. Pat. No. 5,143,854 and PCT patent publication Nos. WO 90/15070 and 92/10092, each of which is incorporated by reference for all purposes. The oligonucleotide probes on the DNA probe array are used to detect complementary nucleic acid sequences in a sample nucleic acid of interest (the "target" nucleic acid).

For sequence checking applications, the chip may be tiled for a specific target nucleic acid sequence. As an example, the chip may contain probes that are perfectly complementary to the target sequence and probes that differ from the target sequence by a single base mismatch. For de novo sequencing applications, the chip may include all the possible probes of a specific length. The probes are tiled on a chip in rows and columns of cells, where each cell includes multiple copies of a particular probe. Additionally, "blank" cells may be present on the chip which do not include any probes. As the blank cells contain no probes, labeled targets should not bind specifically to the chip in this area. Thus, a blank cell provides a measure of the background intensity.

While the Human Genome Project is attempting to produce the first complete reference sequence of the human chromosomes, attention is already focusing on the sequence variations among individuals. The genetic diversity is of interest because it may explain the basis of heritable variation in disease susceptibility, as well as harboring a record of human genetic migrations.

The most common type of human genetic variation is the single-nucleotide polymorphism (SNP), which is a position where two alternative bases occur at appreciable frequency (e.g., greater than 1%) in the human population. There are many uses for SNPs including serving as genetic markers for identifying disease genes by linkage studies in families, linkage disequilibrium in isolated populations, association analysis of patients and controls, and loss-of-heterozygosity studies in tumors to name a few. It is believed that large collections of mapped SNPs would provide a powerful tool for human genetic studies. Although individual SNPs can be less informative than conventional genetic markers, SNPs can be more abundant and have a greater potential for automation.

Accordingly, there is a need for innovative techniques for identifying, confirming, mapping, and categorizing polymers, such as nucleic acids.

SUMMARY OF THE INVENTION

The present invention provides innovative systems and methods for identifying, confirming, mapping, and categorizing polymers, such as nucleic acids. Samples of polymers can be analyzed to determine estimations of the fractions of distinct polymers in the samples. The estimations can then be clustered in order to form a fraction pattern. The fraction pattern can be utilized to interpret data from subsequent samples in order to more accurately identify, confirm, map, and/or categorize the polymers in these samples. Several embodiments of the invention are described below.

In one embodiment, the invention provides a method of estimating a fraction of first and second polymers in a sample of polymers. A first hybridization value indicative of hybridization affinity of the sample of polymers to polymer probes that are complementary to the first polymer is input. A second hybridization value indicative of hybridization affinity of the sample of polymers to polymer probes that are complementary to the second polymer is input. The estimation of the fraction the first and second polymers in the sample of polymers is calculated by dividing the first hybridization value by a sum of the first and second hybridization values.

In another embodiment, the invention provides a method of estimating a fraction of alleles in a sample of nucleic acids. A first hybridization value indicative of hybridization affinity of the sample of nucleic acids to nucleic acid probes that are complementary to a portion of a first allele is input. A second hybridization value indicative of hybridization affinity of the sample of nucleic acids to nucleic acid probes that are complementary to a portion of a second allele is input. The estimation of the fraction of the first and second alleles in the sample of nucleic acids is calculated by dividing the first hybridization value by a sum of the first and second hybridization values.

In another embodiment, the invention-provides a method of genotyping a sample of nucleic acids. Multiple estimations of the fraction of first and second alleles in multiple samples of nucleic acids are generated. The multiple estimations are clustered to form a fraction pattern. An estimation of the fraction of the first and second alleles in a sample of nucleic acids is calculated and the sample of nucleic acids is genotyped by comparing the estimation of the fraction of the first and second alleles in the sample of nucleic acids to the fraction pattern. As an example, the clusters in the fraction pattern can represent homozygous for a first allele, homozygous for a second allele or heterozygous for both alleles.

Other features and advantages of the invention will become readily apparent upon review of the following detailed description in association with the accompanying drawings.

BRIEF DESCRIPTION OF THE DRAWINGS

FIG. 5 illustrates a portion of one embodiment of a genotyping chip.

FIG. 8 is a table of experimental data and results from one embodiment of the invention.

DETAILED DESCRIPTION OF PREFERRED EMBODIMENTS

In the description that follows, the present invention will be described in reference to preferred embodiments that utilize VLSIPS™ technology for making very large arrays of oligonucleotide probes on chips. However, the invention is not limited to nucleic acids or to this technology and may be advantageously applied to other polymers and manufacturing processes. Therefore, the description of the embodiments that follows for purposes of illustration and not limitation.

Figure 1:
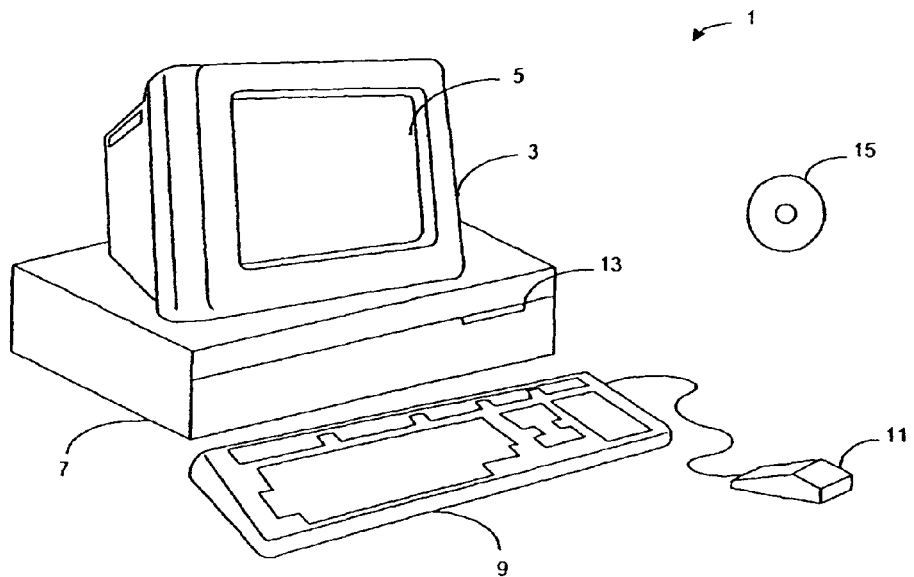
FIG. 1 illustrates an example of a computer system that may be utilized to execute the software of an embodiment of the invention.

FIG. 1 illustrates an example of a computer system that may be used to execute the software of an embodiment of the invention. FIG. 1 shows a computer system 1 that includes a display 3, screen 5, cabinet 7, keyboard 9, and mouse 11. Mouse 11 may have one or more buttons for interacting with a graphical user interface. Cabinet 7 houses a CD-ROM drive 13, system memory and a hard drive (see FIG. 2) which may be utilized to store and retrieve software programs incorporating computer code that implements the invention, data for use with the invention, and the like. Although a CD-ROM 15 is shown as an exemplary computer readable storage medium, other computer readable storage media including floppy disk, tape, flash memory, system memory, and hard drive may be utilized. Additionally, a data signal embodied in a carrier wave (e.g., in a network including the Internet) may be the computer readable storage medium.

Figure 2:
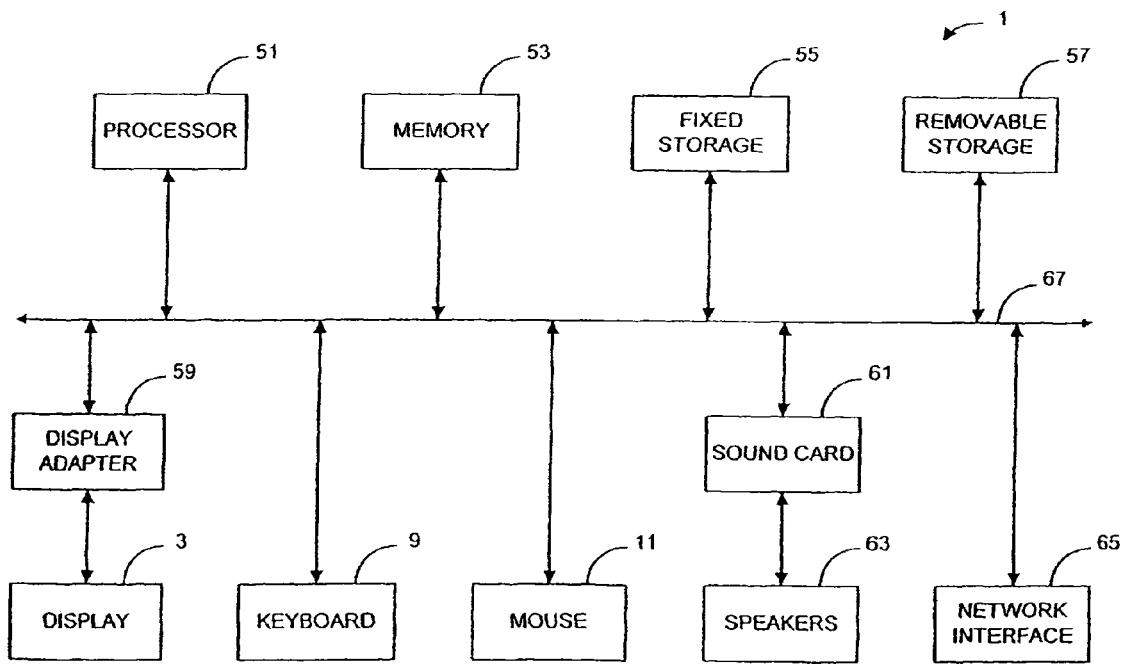
FIG. 2 illustrates a system block diagram of the computer system of FIG. 1.

FIG. 2 shows a system block diagram of computer system 1 used to execute the software of an embodiment of the invention. As in FIG. 1, computer system 1 includes monitor 3 and keyboard 9, and mouse 11. Computer system 1 further includes subsystems such as a central processor 51, system memory 53, fixed storage 55 (e.g., hard drive), removable storage 57 (e.g., CD-ROM drive), display adapter 59, sound card 61, speakers 63, and network interface 65. Other computer systems suitable for use with the invention may include additional or fewer subsystems. For example, another computer system could include more than one processor 51 (i.e., a multi-processor system) or a cache memory.

The system bus architecture of computer system 1 is represented by arrows 67. However, these arrows are illustrative of any interconnection scheme serving to link the subsystems. For example, a local bus could be utilized to connect the central processor to the system memory and display adapter. Computer system 1 shown in FIG. 2 is but an example of a computer system suitable for use with the invention. Other computer architectures having different configurations of subsystems may also be utilized.

For purposes of illustration, the present invention is described as being part of a computer system that designs a chip mask, synthesizes the probes on the chip, labels the nucleic acids, and scans the hybridized nucleic acid probes. Such a system is fully described in U.S. Pat. No. 5,571,639 that has been incorporated by reference for all purposes. However, the present invention may be used separately from the overall system for analyzing data generated by such systems.

Figure 3:
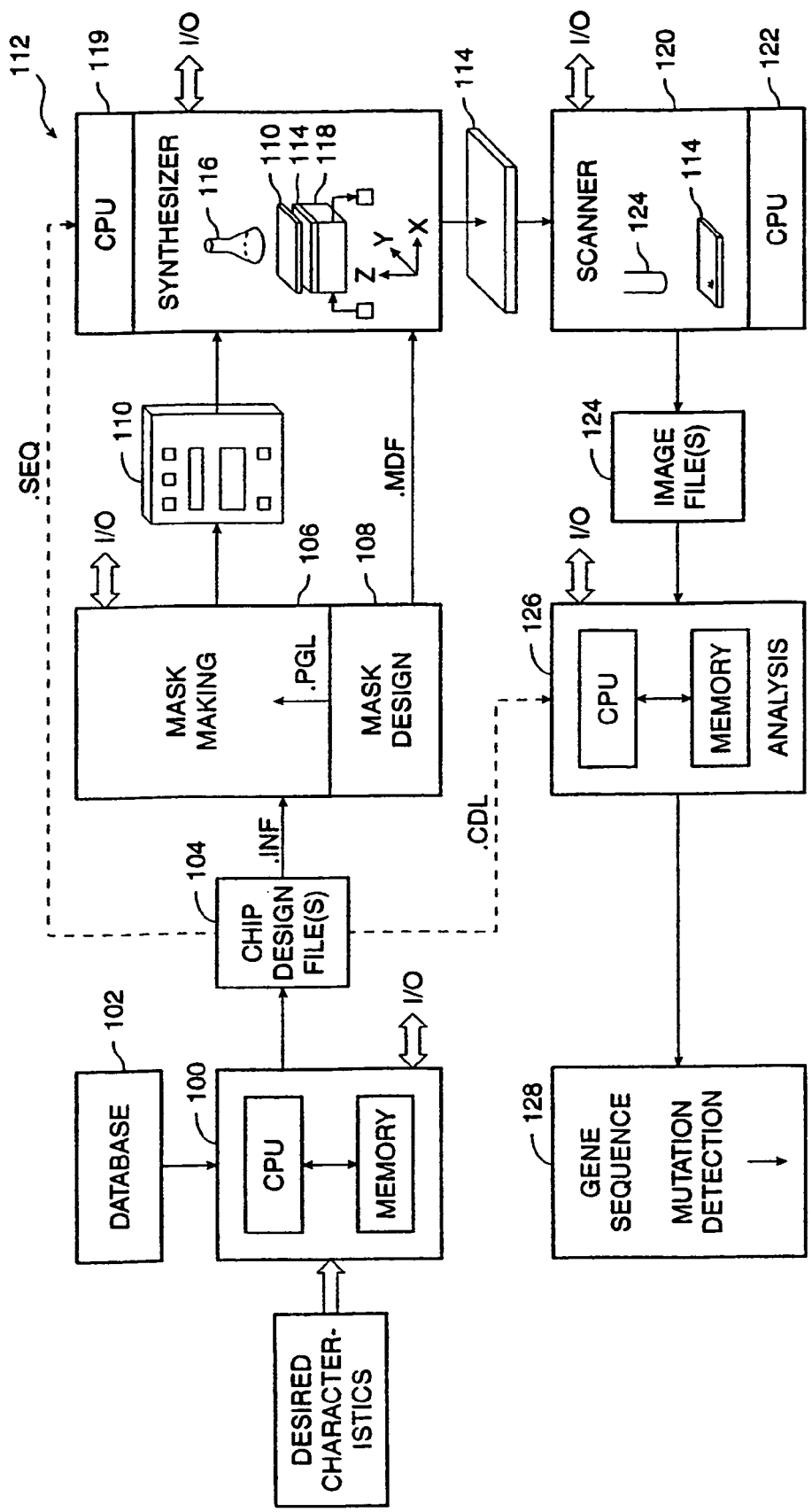
FIG. 3 illustrates an overall system for forming and analyzing arrays of biological materials such as DNA or RNA.

FIG. 3 illustrates a computerized system for forming and analyzing arrays of biological materials such as RNA or DNA. A computer 100 is used to design arrays of biological polymers such as RNA and DNA The computer 100 may be, for example, an appropriately programmed Sun Workstation or personal computer or workstation, such as an IBM PC equivalent, including appropriate memory and a CPU as shown in FIGS. 1 and 2. The computer system 100 obtains inputs from a user regarding characteristics of a gene of interest, and other inputs regarding the desired features of the array. Optionally, the computer system may obtain information regarding a specific genetic sequence of interest from an external or internal database 102 such as GenBank. The output of the computer system 100 is a set of chip design computer files 104 in the form of, for example, a switch matrix, as described in PCT application WO 92/10092, and other associated computer files.

The chip design files are provided to a system 106 that designs the lithographic masks used in the fabrication of arrays of molecules such as DNA. The system or process 106 may include the hardware necessary to manufacture masks 110 and also the necessary computer hardware and software 108 necessary to lay the mask patterns out on the mask in an efficient manner. As with the other features in FIG. 3, such equipment may or may not be located at the same physical site but is shown together for ease of illustration in FIG. 3. The system 106 generates masks 110 or other synthesis patterns such as chrome-on-glass masks for use in the fabrication of polymer arrays.

The masks 110, as well as selected information relating to the design of the chips from system 100, are used in a synthesis system 112. Synthesis system 112 includes the necessary hardware and software used to fabricate arrays of polymers on a substrate or chip 114. For example, synthesizer 112 includes a light source 116 and a chemical flow cell 118 on which the substrate or chip 114 is placed. Mask 110 is placed between the light source and the substrate/chip, and the two are translated relative to each other at appropriate times for deprotection of selected regions of the chip. Selected chemical regents are directed through flow cell 118 for coupling to deprotected regions, as well as for washing and other operations. All operations are preferably directed by an appropriately programmed computer 119, which may or may not be the same computer as the computer(s) used in mask design and mask making.

The substrates fabricated by synthesis system 112 are optionally diced into smaller chips and exposed to marked targets. The targets may or may not be complementary to one or more of the molecules on the substrate. The targets are marked with a label such as a fluorescein label (indicated by an asterisk in FIG. 3) and placed in scanning system 120. Although preferred embodiments utilize fluorescent markers, other markers may be utilized that provide differences in radioactive intensity, light scattering, refractive index, conductivity, electroluminescence, or other large molecule detection data. Therefore, the present invention is not limited to analyzing fluorescence measurements of hybridization but may be readily utilized to analyze other measurements of hybridization.

Scanning system 120 again operates under the direction of an appropriately programmed digital computer 122, which also may or may not be the same computer as the computers used in synthesis, mask making, and mask design. The scanner 120 includes a detection device 124 such as a confocal microscope or CCD (charge-coupled device) that is used to detect the location where labeled target (*) has bound to the substrate. The output of scanner 120 is an image file(s) 124 indicating, in the case of fluorescein labeled target, the fluorescence intensity (photon counts or other related measurements, such as voltage) as a function of position on the substrate. Since higher photon counts will be observed where the labeled target has bound more strongly to the array of polymers (e.g., DNA probes on the substrate), and since the monomer sequence of the polymers on the substrate is known as a function of position, it becomes possible to determine the sequence(s) of polymer(s) on the substrate that are complementary to the target.

The image file 124 is provided as input to an analysis system 126 that incorporates the synthesis integrity evaluation techniques of the present invention. Again, the analysis system may be any one of a wide variety of computer system(s), but in a preferred embodiment the analysis system is based on a WINDOWS NT workstation or equivalent. The analysis system may analyze the image file(s) to generate appropriate output 128, such as the identity of specific mutations in a target such as DNA or RNA.

Figure 4:
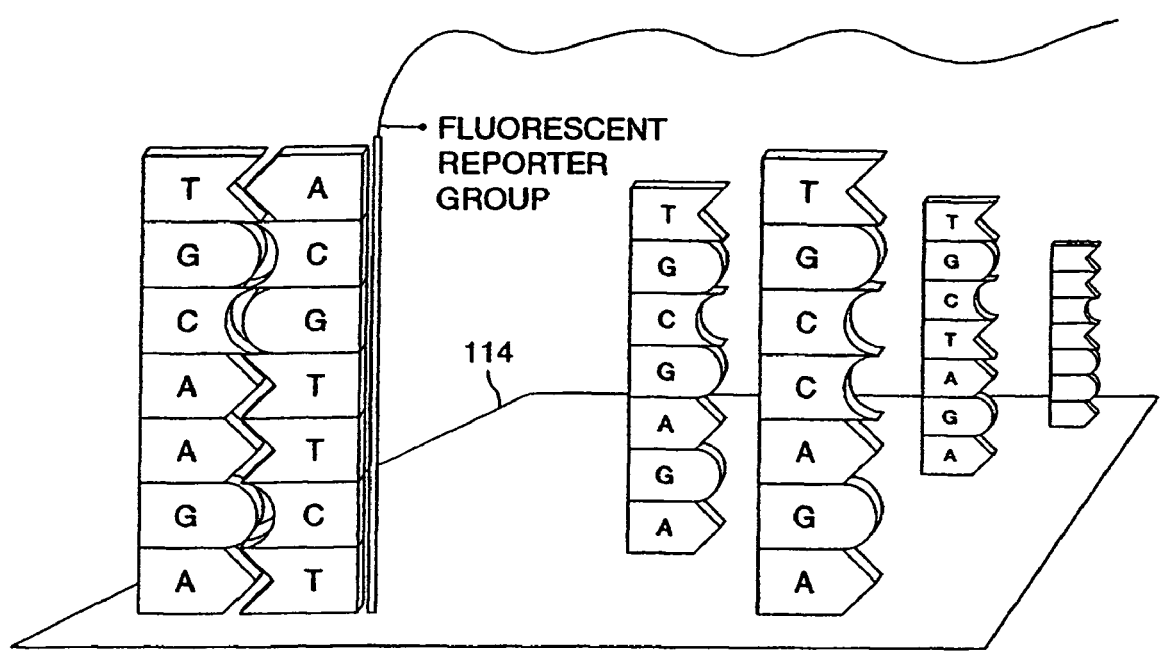
FIG. 4 illustrates conceptually the binding of probes on chips.

FIG. 4 illustrates the binding of a particular target DNA to an array of DNA probes 114. As shown in this simple example, the following probes are formed in the array:

```
3'-AGAACGT

AGACCGT

AGAGCGT

AGATCGT

●

●

●
```

As shown, when the fluorescein-labeled (or otherwise marked) target 5'-TCTTGCA is exposed to the array, it is complementary only to the probe 3'-AGAACGT, and fluorescein will be primarily found on the surface of the chip where 3'-AGAACGT is located. The chip contains cells that include multiple copies of a particular probe and the cells may be square regions on the chip.

In the description that follows, the invention will be described in reference to SNPs. Therefore, at these SNP positions, the sample nucleic acids can generally include one or both of two alleles, which will be referred to generically as the A-allele and the B-allele. In a pool of individuals, it would be expected that if there is an SNP at a location, some individuals would be homozygous AA, some would be homozygous BB and some would be heterozygous AB. Although the invention will be described in reference to SNPs, the invention is not so limited and can be advantageously applied to other polymorphism conditions including insertions, deletions, multi-position polymorphisms, multi-base polymorphisms, and multi-allelic positions.

FIG. 5 shows a portion of a tiled chip that can be utilized to identify, confirm, map, and/or genotype sample nucleic acids. The chip typically includes thousands of cells where nucleic acid probes are coupled to the chip. The chip can have different probes filed on the chip for a specific applications (e.g., detecting mutations that are indicative of a change in resistance to a drug therapy in treating HIV) or the chips can be generic (e.g., have all possible 8-mer probes). Furthermore, the cells can be laid out on the chip in any number of ways. For example, the cells can be tiled in locations to improve scan data by reducing inter-cell interference, to reduce the cost of manufacturing by decreasing the number of masks utilized, or to make it easier for users to interpret the data.

A preferred layout of a portion of genotyping chip will be described in reference to FIG. 5. The layout is generally organized so it is easier for users to interpret the data and understand the structure of the probes on the chip as will be described herein. However, it should be understood that the invention is not limited to any specific chip layout or structure of the probes. The invention can be advantageously applied to other chip layouts as well.

Assume that the A-allele includes the sequence 5'-CCTC GGCAT and the B-allele includes the sequence 5'-CCTC AGCAT, where the underlined nucleotide represents the SNP that distinguishes the alleles. For discussion purposes, the position of nucleotides in the alleles will be specified by the variable d, where d=0 for the SNP and d decreases to the left of the SNP and increases to the right of the SNP. FIG. 5 shows a block 201 that includes five positions around the SNP. The number of positions included in block 201 has been chosen for illustration purposes and can be varied depending on the application.

Along the top of FIG. 5 is shown the sequence of the alleles. At d=0, the nucleotide is shown as G/A to represent the SNP that distinguishes the A-allele and the B-allele. As shown, block 201 includes four rows of cells tiled for the A-allele and four rows of cells tiled for the B-allele. The rows of cells are designed by nucleotides T, G, A, and A, which represent the nucleotide at the interrogation position of the nucleic acid probes in that row. Block 201 can be further divided into miniblocks 203, which represent a set of cells (and their corresponding probes) that have a perfect match probe for the alleles of interest and zero or more mismatch probes. Although the miniblocks are shown as columns on the chip in one embodiment, they are not required to be in any particular spatial orientation on the chip.

Recalling that the sequence of the alleles is 5'-CCTC ?GCAT where the question mark indicates that the SNP that can be either a G or A. Assuming that the probes on the chip are 5-mers with an interrogation position at the center nucleotide, the probes on the chip would be as follows:

| d        | -2    | -1    | 0     | 1     | 2     |
|----------|-------|-------|-------|-------|-------|
| A-allele | GGTGC | GATCC | AGTCG | GCTGT | CCTTA |
|          | GGGGC | GAGCC | AGGCG | GCGGT | CCTTA |
|          | GGCGC | GACCC | AGCCG | GCCGT | CCTTA |
|          | GGAGC | GAACC | AGACG | GCAGT | CCTTA |
|          |       |       |       |       |       |
| B-allele | GGTGT | GATTC | AGTCG | GTTGT | TCTTA |
|          | GGGGT | GAGTC | AGGCG | GTGGT | TCTTA |
|          | GGCGT | GACTC | AGCCG | GTCGT | TCTTA |
|          | GGAGT | GAATC | AGACG | GTAGT | TGTTA |

The interrogation position nucleotides are underlined in the probes. Additionally, the SNP nucleotides are bolded in each probe: C in the case of the A-allele and T in the case of the B-allele. As shown, the miniblock at d=0 has two identical halves, accordingly it would be possible to only tile one half of the miniblock at that location.

The miniblocks shown include a perfect match (i.e., a probe perfectly complementary to the target allele) to the target alleles and multiple probes with a single mismatch. The center miniblocks are unique in that the interrogation position is the same as the SNP. Accordingly, the mismatch probes of the center miniblock have a single base mismatch from both of the alleles. This is in contrast to the noncenter miniblocks where the mismatch probes have a single base mismatch to one allele and two base mismatches from the other allele.

Returning to FIG. 5, the cells are labeled with the following:

PMa—perfect match to A-allele
PMb—perfect match to B-allele
Ma—single base mismatch to A-allele
Mb—single base mismatch to B-allele
M*—single base mismatch to both the A-allele and B-allele FIG. 5 illustrates that the noncenter miniblocks include two perfect match probes and four mismatch probes, two for each allele. The center miniblocks include perfect-match probes for each allele and two mismatch probes for both alleles. In the discussion that follows, these labels will be utilized to describe embodiments of the invention.

Figure 6:
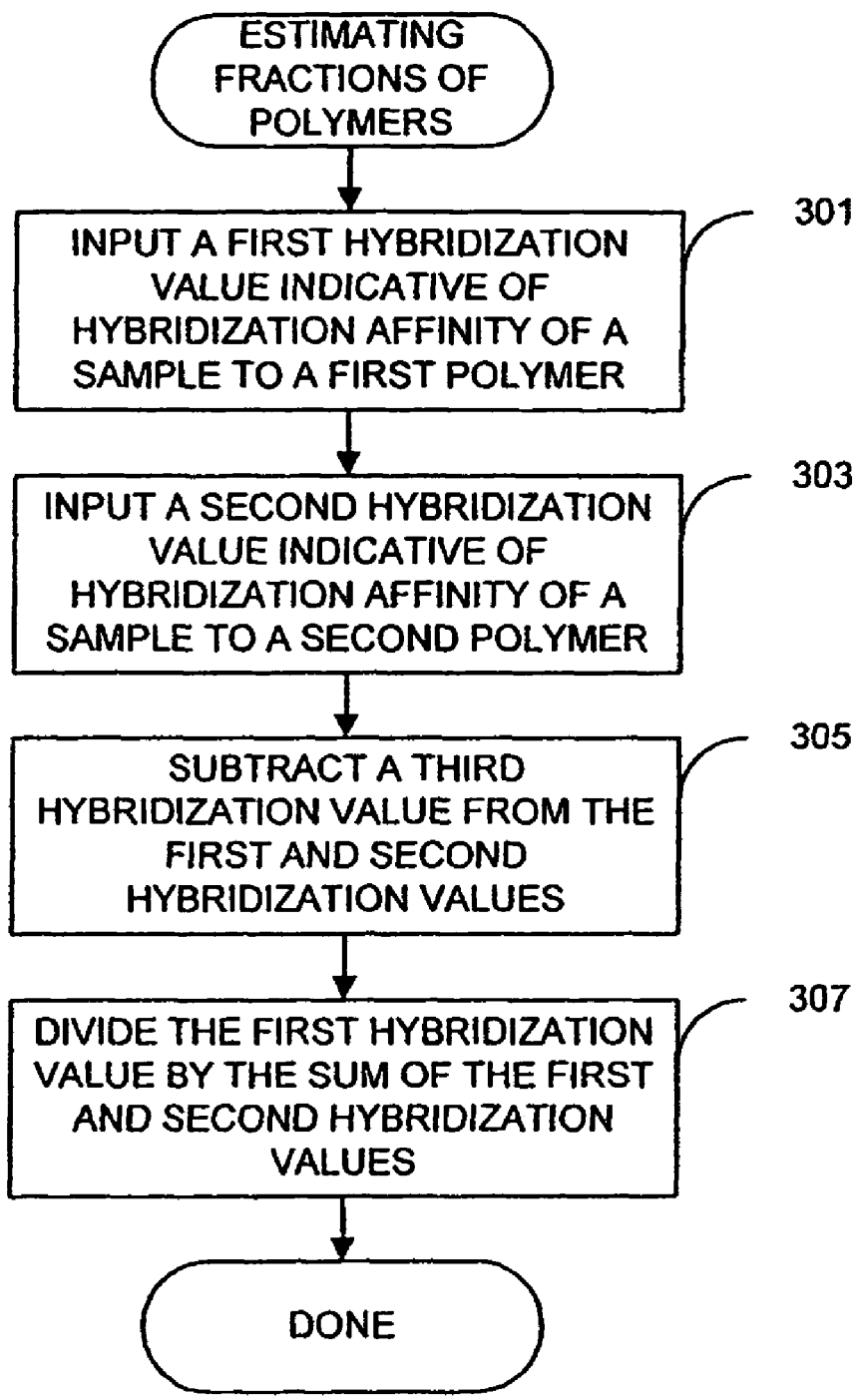
FIG. 6 shows a flowchart of a process of estimating fractions of polymers.

FIG. 6 is a flowchart of a estimating fractions of polymers in a sample having multiple polymers. Although in preferred embodiments, the polymers are nucleic acids, other polymers including peptides, oligosaccharides and the like can be utilized. Therefore, the invention is not limited to the specific embodiments described herein.

At a step 301, a first hybridization value indicative of hybridization affinity of a sample of polymers to a first polymer is input. The sample of polymers can have multiple different sequences of polymers including those that are complementary to the first polymer. A second hybridization value indicative of hybridization affinity of a sample of polymers to a first polymer is input at a step 303. The first and second hybridization values are expected to vary according to the fraction of the sample of polymers that are complementary to the first and second polymer.

At a step 305, a third hybridization value is subtracted from the first and second hybridization values. The third hybridization value can be utilized to normalize the first and second hybridization values. As will be described below, in preferred embodiments, the third hybridization value is derived from mismatched nucleic acid probes, which can make subtracting a background value unnecessary.

An estimation of the fraction of the first and second polymers in the sample of polymers is calculated by dividing the first normalized hybridization value by the sum of the first and second normalized hybridization values. In this manner, the estimation will generally vary between 0 and 1, where 1 indicates a very high concentration of polymers complementary to the first polymer and 0 indicates a very high concentration of polymers complementary to the second polymer.

In embodiments where more than one polymer or allele is being analyzed, the denominator can include three or more hybridization values. Accordingly, the invention is not limited to analyzing only two polymers or alleles.

Returning back to the labels of the nucleic acid probes of a preferred embodiment, it would be expected that if a sample of nucleic acid probes was taken from an individual that was homozygous for the A-allele, then PMa>PMb=M* at the center miniblock. Similarly, it would be expected that if a sample of nucleic acid probes was taken from an individual that was homozygous for the B-allele, then PMb>PMa=M* at the center miniblock. If the individual was heterozygous, it would be expected that PMa≅PMb>M* at the center miniblock.

The estimation of the fraction shown in FIG. 6 can be as follows for each of the miniblocks:

$$p\text{-hat}=(PMa-MM)/(PMa-MM)+(PMb-MM)$$

where p-hat represents the estimation of the fraction and MM is derived from the mismatch probes M*, Ma or Mb. As an example, MM can be calculated as follows:

$$MM=\min(M^*,M^*) \text{ for the center miniblocks}$$

$$MM=\max(\text{median}(Ma,Ma,Ma), \text{median}(Mb,Mb,Mb))$$
for the noncenter miniblocks The minimum is utilized for center miniblocks in one embodiment because there are only two distinct M* mismatch probes and it can be desirable to avoid including a very large value that could result from cross-hybridization events.

The above equations for MM are illustrative of those that can be utilized. Others can be utilized and may be preferably varied depending on the specific application. As an example, the miniblocks can be tiled with only one mismatch probe. In such a case, MM can be equal to the hybridization affinity measured from probes in the single mismatch cell. Although mismatch probes are not required, they have been found to make the calculations more robust.

It will be apparent from looking at the above equation for p-hat that if PMa or PMb is less than MM, p-hat can become negative and possibly result in a division by zero. Accordingly, in some embodiments, if a calculation of (PMa−MM) or (PMb−MM) results in a negative number, the result is set equal to zero. Accordingly, if Da=max(PMa−MM, 0) and Db=max(PMb−MM, 0), the above p-hat formula can be written as follows:

$$p\text{-hat}=Da/(Da+Db)$$

It would still be possible to have a denominator of zero, but as will be described in more detail later, a quality filter can reject such data as bad so the illegal operation does not occur. Another alternative would be to set a negative (or zero) result to a very small number like 0.00001, as an example.

In another embodiment, the fraction estimation can be calculated from multiple miniblocks. For example, the hybridization affinity of the perfect match probes PMa from the miniblocks can be summed and the hybridization affinity of the perfect match probes PMb from the miniblocks can be summed. The sums are then utilized in one of the above formulas as PMa and PMb, respectively, to produce the fraction estimation p-hat. One advantage of this embodiment is that the miniblocks are effectively weighted according to the hybridization affinities of the perfect match probes, which can be desirable in some applications.

Figure 7:
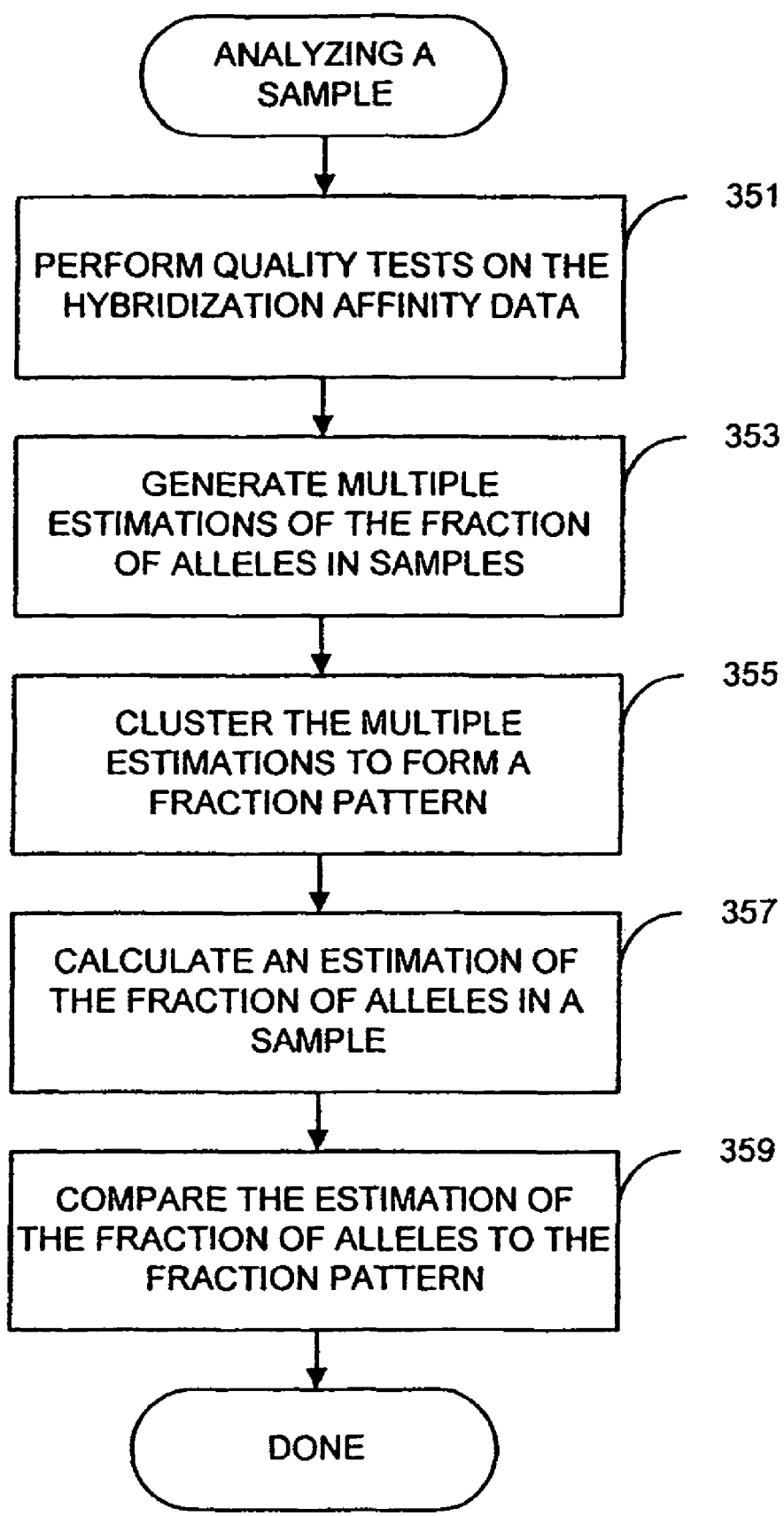
FIG. 7 shows a flowchart of a process of analyzing a sample of nucleic acids.

FIG. 7 shows a flowchart of a process of analyzing a sample of multiple nucleic acids. At a step 351, quality tests are performed on the hybridization affinity data. As in all the flowcharts herein, there are many steps that can be deleted, added, combined, and modified while still being within the spirit of the invention. Quality tests are not required in all embodiments but they can be beneficial in removing hybridization affinity data that are erroneous (e.g., there is a flaw in the chip or an error occurred while scanning a region of the hybridized chip). One quality test that can be utilized is that (PMa−MM) and (PMb−MM) must be above some predetermined threshold (e.g., 15 photon counts). Another quality test can be the highest hybridization affinity must be from a perfect match probe PMa or PMb.

Another quality test can be if (PMa/max(Ma)<1 and (PMb/max(Mb)<1, then the miniblock fails. Other quality tests can be devised and utilized. Additionally, the quality tests can be combined so that more than one must be passed for further processing. Quality tests can also be performed on blocks as a whole if desired.

Multiple estimations of the fraction of alleles in samples are generated at a step 353. Each estimation of the fraction of nucleic acids in a sample can be calculated according to the process shown in FIG. 6 or described above. The samples can be taken from a reasonably large and diverse group of individuals. The multiple estimations of the fraction of alleles in the samples are clustered to form a fraction pattern at a step 355. The clustering can be performing in a conventional manner including the valley seeking clustering techniques described by W. L. G. Koontz et al. IEEE Trans., Comp. C-21, 171 (1972), which is hereby incorporated by reference. Other clustering techniques can be utilized with the invention. As the following will describe, the fraction pattern can be subsequently utilized for identifying, confirming, mapping, and/or genotyping samples of nucleic acids.

At a step 357, a sample is analyzed and an estimation of the fraction of alleles in the sample is calculated. The estimation can be calculated according to the process shown in FIG. 6 and described above. The estimation of the fraction of alleles is compared to the fraction pattern at a step 359. The comparison can result in identifying an SNP, confirming its existence, mapping the target, and/or genotyping the sample (or individual from which it was obtained).

It may be beneficial to now describe data from an experiment performed with an embodiment of the invention. A genotyping chip having a structure similar to that described in reference to FIG. 5 was hybridized to samples from 41 individuals. The chip included approximately 600 SNPs. FIG. 8 shows a tabular summary of the results of the experiment for the first 45 SNPs.

A table 375 includes multiple columns of which column 376 is the number of the SNP (here 1-45) that is depicted in the designated row of the table. Column 377 is the name of the SNP (or marker). Although to reduce confusion, the nucleic acids have been discussed as though there was only one direction, preferred embodiments utilize sample nucleic acids and probes of both the sense and antisense strands. Column 378 specifies from which strand the data represents with "A" representing sense and "Z" representing antisense.

Column 379 depicts the number of samples that were not utilized for the particular SNP (e.g., the data did not pass a quality filter). Column 380 indicates the number of individuals that are homozygous AA, column 381 indicates the number of individuals that are heterozygous AB, and column 382 indicates the number of individuals that are homozygous BB. Column 383 indicates the center of the clusters in the fraction pattern that corresponds to the homozygous AA individuals, column 384 indicates the center of the clusters in the fraction pattern that corresponds to the heterozygous AB individuals, and column 385 indicates the center of the clusters in the fraction pattern that corresponds to the homozygous BB individuals. The estimations of the fractions were multiplied by 100 to give values for the fraction pattern that range from approximately 0 to 100 as shown for convenience.

It may be expected that the center of the clusters for homozygous AA individuals would be at 100, the center of the clusters for the heterozygous AB individuals would be at 50, and the center of the clusters for homozygous BB individuals would be at 0. A perusal of table 375 shows that this is rarely the case with real data. A row 391 shows very good data in that the center of the clusters for columns 383-385 is at 99, 48 and 1, which is very close to what one might expect. However, a row 393 includes data where the center of the clusters for columns 383-385 is at 97, 71 and 10, which is very different from what one would probably expect.

Data like that shown in row 393 illustrates that it may not be entirely accurate to genotype according to a strict 100, 50 and 0 scale. The fraction pattern may be unique for each SNP. For example, the fraction pattern may be the result of the specific nucleic acid sequences near the SNP, the interaction of the nucleic acids during hybridization and the like. In order to genotype a sample (or individual) at the SNP corresponding to row 393, embodiments of the invention utilize the fraction pattern of 97, 71 and 10. Accordingly, if the estimation of the fraction of alleles in the sample is within a predefined range of 71, the sample is genotyped as heterozygous. Thus, an estimation of 75 could result in a genotype call of heterozygous, whereas using a 100, 50 and 0 scale may likely result in noncall or an erroneous call.

The existence and relative positions of three clusters can be utilized to identify and/or confirm SNPs. SNPs can also be identified and confirmed according to the innovative techniques describe in U.S. patent application Ser. No. 09/134,758, filed Aug. 14, 1998, which is hereby incorporated by reference. Other techniques can be utilized to identify and confirm SNPs including conventional gel-based techniques.

A row 395 shows only two clusters, as there is no cluster for homozygous BB. This could be the result of not having a sample from an individual that is homozygous BB. However, unusual clustering patterns can also demonstrate that there is not an SNP at that position or that a more complex mutation is occurring. For example, a single cluster can indicate that there is not an SNP at that position, whereas a clustering of more than three cluster can be indicative of more differences in the nucleic acids than a single polymorphism.

Figure 9A:
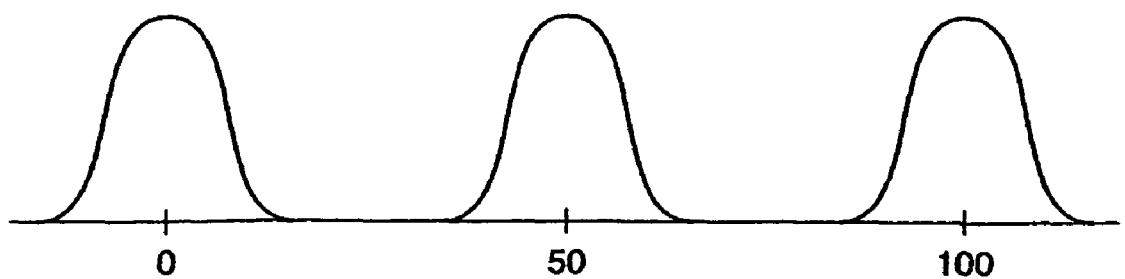
FIG. 9A-9C illustrate fraction patterns from the table of FIG. 8.
Figure 9B:
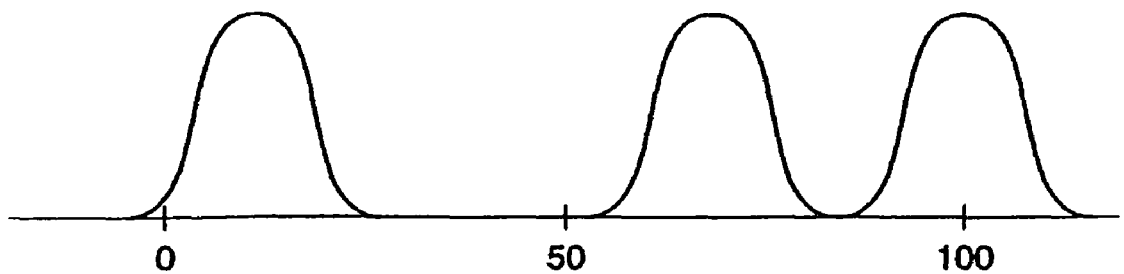
Figure 9C:
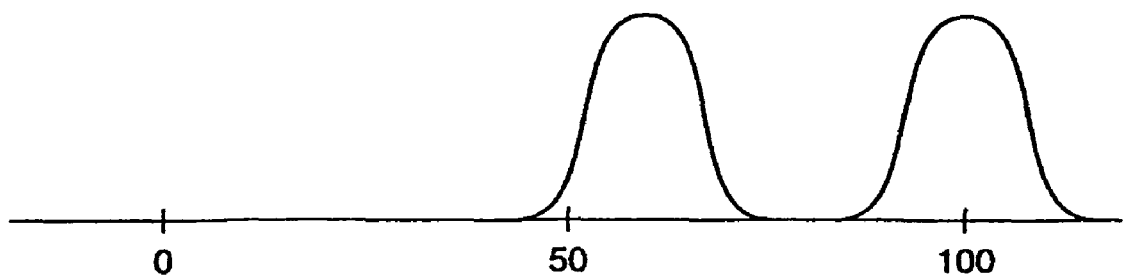

FIGS. 9A-9C illustrate the fraction patterns of rows 391, 393 and 395, respectively. As shown, FIG. 9A looks to be almost ideal (i.e., expected) in that the clusters are well spaced apart. However, FIG. 9B shows a fraction pattern that has two clusters fairly close together. And lastly, FIG. 9C shows a fraction pattern that only has two clusters. The sizes of the clusters do not depict the relative number of samples within the cluster but are shown to illustrate to the reader how different the center of the clusters can be and how the fraction patterns can vary depending on the SNP.

The relative change in fraction patterns for an individual can be monitored over time. For example, a tumor causing SNP can be monitored to determine if the relative concentrations of the allele believed responsible for the tumor is decreasing with therapy.

Figure 10:
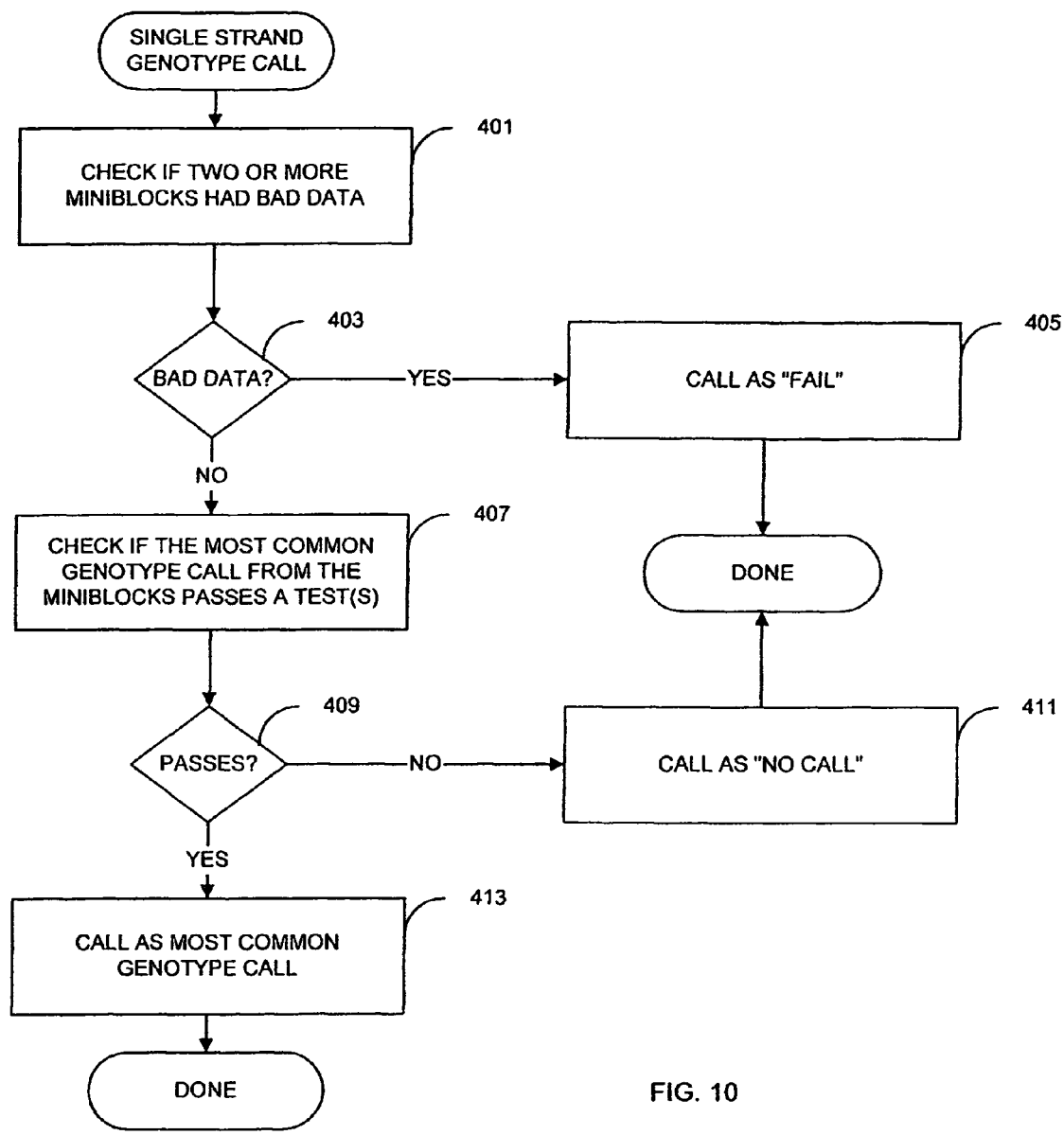
FIG. 10 shows a flowchart of a process of making a genotype call form a single strand.

FIG. 10 shows a flowchart of a process of making a single strand genotype call. At a step 401, a check can be performed to determine if two or more miniblocks had bad data. For example, two or more miniblocks for the SNP did not pass a quality test of step 351 of FIG. 7. If there was two or more miniblocks with bad data at a step 403, the genotype call is "fail" at a step 405. Otherwise, a check can be performed to determine if the most common genotype call from the miniblocks passes a test or tests at a step 407. Although the check in step 401 has been described in reference to two or more miniblocks, this number can be varied in depending on the application. However, it may be beneficial if the number of miniblocks for the test is varied proportionally with the number of miniblocks (i.e., if the number of miniblocks increases, so does the number involved in the check).

A test be $n>(N-s)/2$, where N is equal to the number of miniblocks, n is the number of miniblocks making the most common genotype call and s is the number of miniblocks that had bad data or did not pass a quality test. Another test can be $m<2$, where m is equal to the number of miniblocks making the second most common genotype call. Additionally, a test can be $n-m\geq(N-s)/2$. If the miniblocks fail to pass one or a combination of the tests (e.g., all the equations are true) at a step 409, the genotype call is "no call" at a step 411. Other tests and combinations of tests can also be devised and utilized. If the miniblocks pass the test or tests, the genotype call is the most common genotype call made by the miniblocks at a step 413.

Figure 11:
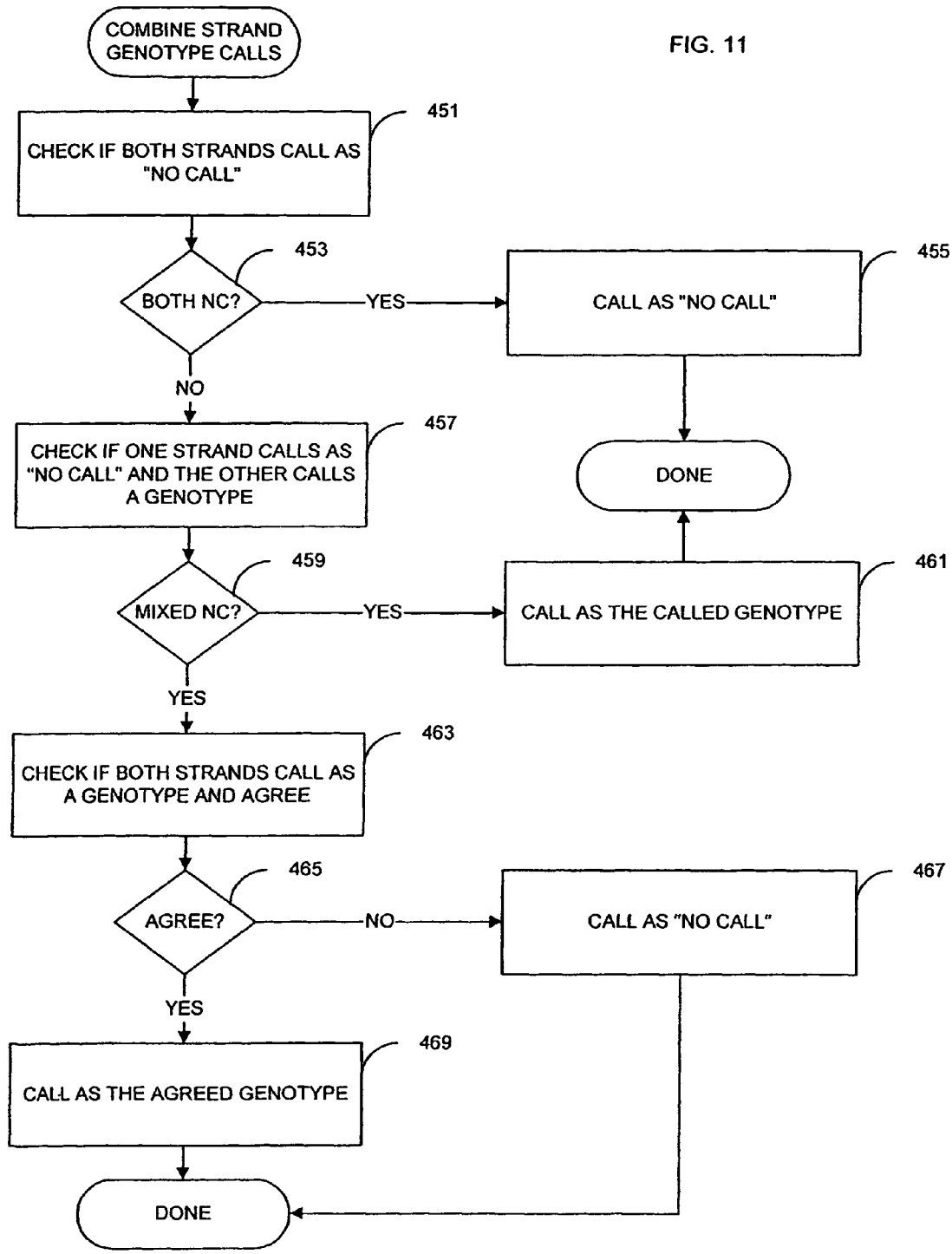
FIG. 11 shows a flowchart of a process of combining strand genotype calls into a single genotype call.

FIG. 11 shows a flowchart of a process of combining strand genotype calls. The multiple strand genotype calls can be made by a process as shown in FIG. 10. For simplicity, the flowchart of FIG. 11 will be described in reference to two strands. However, the process can be advantageously applied to combining genotype calls from more than two strands and to results from different experiments.

At a step 451, a check can be performed to determine if both strands produced a "no call." If both strands did produce a "no call" at a step 453, the combined call is a "no call" at a step 455. Otherwise, a check is performed to determine if one strand produced a "no call" and the other produced a genotype call (e.g., homozygous AA). If the strands had a mixed "no call" result, the genotype call is made at a step 461.

A check is performed at a step 463 to determine if both strands make a genotype call and agree on the call. If both strands do not produce the same genotype call, the call is a "no call" at a step 467. Otherwise, the genotype call for both strands is made as the agreed genotype call at a step 469.

Embodiments of the invention have been utilized to simultaneously genotype 500 SNPs utilizing a single genotyping chip. See "Large-Scale Identification, Mapping, and Genotyping of Single-Nucleotide Polymorphisms in the Human Genome," David G. Wang et al., Science, Vol. 280, pp. 1077-1082, May 15, 1998, which is hereby incorporated by reference. The results demonstrated the feasibility of large-scale identification and analysis of SNPs was possible utilizing embodiments of the invention.

While the above is a complete description of preferred embodiments of the invention, various alternatives, modifications, and equivalents may be used It should be evident that the invention is equally applicable by making appropriate modifications to the embodiments described above. For example, the invention has been described in reference to nucleic acid probes that are synthesized on a chip. However, the invention may be advantageously applied to other monomers (e.g., amino acids and saccharides) and other hybridization techniques including those where the probes are not attached to a substrate. Therefore, the above description should not be taken as limiting the scope of the invention that is defined by the metes and bounds of the appended claims along with their full scope of equivalents.

What is claimed is:

1. A method of estimating a fraction of a first allele and a second allele for each of a plurality of SNP locations, in a sample of nucleic acids, comprising:

inputting for each SNP location, a first hybridization value indicative of hybridization affinity of the sample of nucleic acids to nucleic acid probes that are complementary to the first allele, wherein the first hybridization value is a sum of hybridization values for a plurality of nucleic acid probes that are a perfect match to the first allele;

inputting for each SNP location, a second hybridization value indicative of hybridization affinity of the sample of nucleic acids to nucleic acid probes that are complementary to the second allele, wherein the second hybridization value is a sum of hybridization values for a plurality of nucleic acid probes that are a perfect match to the second allele;

selecting for each SNP location, a third hybridization value that is indicative of hybridization affinity of the sample of nucleic acids to nucleic acid probes that include at least one nucleotide that differs from both the first and second alleles;

providing a normalized first and second hybridization value by subtracting the third hybridization value from the first and second hybridization values; and calculating an estimation of the fraction of the first allele and the second allele in the sample of nucleic acids by dividing the normalized first hybridization value by a sum of the normalized first and second hybridization values, wherein the calculation is performed by a computer comprising a computer software product.

2. The method of claim 1, wherein the normalized first and second hybridization values are set equal to zero if they are less than zero.

3. The method of claim 1, further comprising:

generating a plurality of estimations of the fraction of the first allele and the second allele in a plurality of samples of nucleic acids for each of a plurality of SNP locations; and clustering the plurality of estimations to form a fraction pattern for each SNP location.

4. The method of claim 1, wherein:

wherein the normalized first and second hybridization values are set to 0.00001 if they are less than zero.

5. A computer program product stored in a non-transitory computer readable medium, that estimates a fraction of a first allele and a second allele for each of a plurality of SNP locations, in a sample of nucleic acids, comprising:

computer code that receives for each SNP location, a first hybridization value indicative of hybridization affinity of the sample of nucleic acids to nucleic acid probes that are complementary to the first allele, wherein the first hybridization value is a sum of the hybridization values to a plurality of perfect match nucleic acid probes that are a perfect match to the first allele;

computer code that receives for each SNP location, a second hybridization value indicative of hybridization affinity of the sample of nucleic acids to nucleic acid probes that are complementary to the second allele, wherein the second hybridization value is a sum of the hybridization values to a plurality of perfect match nucleic acid probes that are a perfect match to the second allele; and computer code that calculates for each SNP location, an estimation of the fraction of the first plurality of the first allele and the second plurality of the second allele in the sample of nucleic acids by:
subtracting from the first and second hybridization values a third hybridization value, that is indicative of hybridization affinity of the sample of nucleic acids to nucleic acid probes that include at least one nucleotide that differs from both the first and second alleles for each SNP location, to provide normalized first and second hybridization values; and dividing the first normalized hybridization value by a sum of the normalized first and second hybridization values.

6. The computer program product of claim 5, further comprising:
computer code that stores the calculated estimates of the fraction of the first plurality of the first allele and the second plurality of the second allele in a computer readable storage medium.

* * * * *